United States Patent [19]
Klein

[11] Patent Number: 5,453,010
[45] Date of Patent: Sep. 26, 1995

[54] DENTAL POST WITH INTERNAL RETENTION MEANS

[75] Inventor: Philip B. Klein, Bryn Mawr, Pa.

[73] Assignee: Dental Logics, Inc., Bryn Mawr, Pa.

[21] Appl. No.: 212,623

[22] Filed: Mar. 11, 1994

[51] Int. Cl.$^6$ ..................................... A61C 5/08
[52] U.S. Cl. ........................................... 433/221; 433/220
[58] Field of Search ..................... 433/220, 221, 433/225

[56] References Cited

U.S. PATENT DOCUMENTS

| | | | |
|---|---|---|---|
| 1,397,067 | 11/1921 | Williams | 433/221 |
| 2,536,669 | 1/1951 | Thau-Jensen | 433/221 |
| 4,253,835 | 3/1981 | Ware | 433/220 |
| 4,600,392 | 7/1986 | Weissman | 433/225 |
| 4,622,012 | 11/1986 | Smoler | 433/221 |
| 4,752,225 | 6/1988 | Bori | 433/221 |
| 4,778,388 | 10/1988 | Yuda et al. | 433/221 |
| 4,846,685 | 7/1989 | Martin | 433/221 |
| 4,934,936 | 6/1990 | Miller | 433/220 |
| 5,073,112 | 12/1991 | Weil | 433/221 |
| 5,094,618 | 3/1992 | Sullivan | 433/173 |
| 5,161,973 | 11/1992 | Johnson | 433/221 |

FOREIGN PATENT DOCUMENTS 312611  3/1956  Switzerland .................. 433/221

*Primary Examiner*—Cary E. O'Connor
*Attorney, Agent, or Firm*—Caesar, Rivise, Bernstein, Cohen & Pokotilow, Ltd.

[57] ABSTRACT

A dental post for securely retaining a dental restoration on a prepared tooth stub having a top surface and a bore extending therein. The dental post comprises a bulbous head and a shank. The shank is an elongated rod-like member having a first longitudinal axis, with the outside diameter of the shank measured along a second axis perpendicular to the first axis and being a predetermined dimension. The shank is arranged to be fixedly secured within the bore so that the bulbous head extends beyond the top surface of the prepared tooth stub. The bulbous head has an outside diameter measured along a third axis parallel to the second axis and is a predetermined dimension. The bulbous head has plural through passageways, e.g., a coronal passageway, and a transverse passageway that communicate with one another. The plural through passageways are for receipt of a setable securement medium which flows therein and about the surface of the head to secure the dental restoration to the post. A dental pliers is also disclosed for the safe handling and insertion of the dental post.

13 Claims, 3 Drawing Sheets

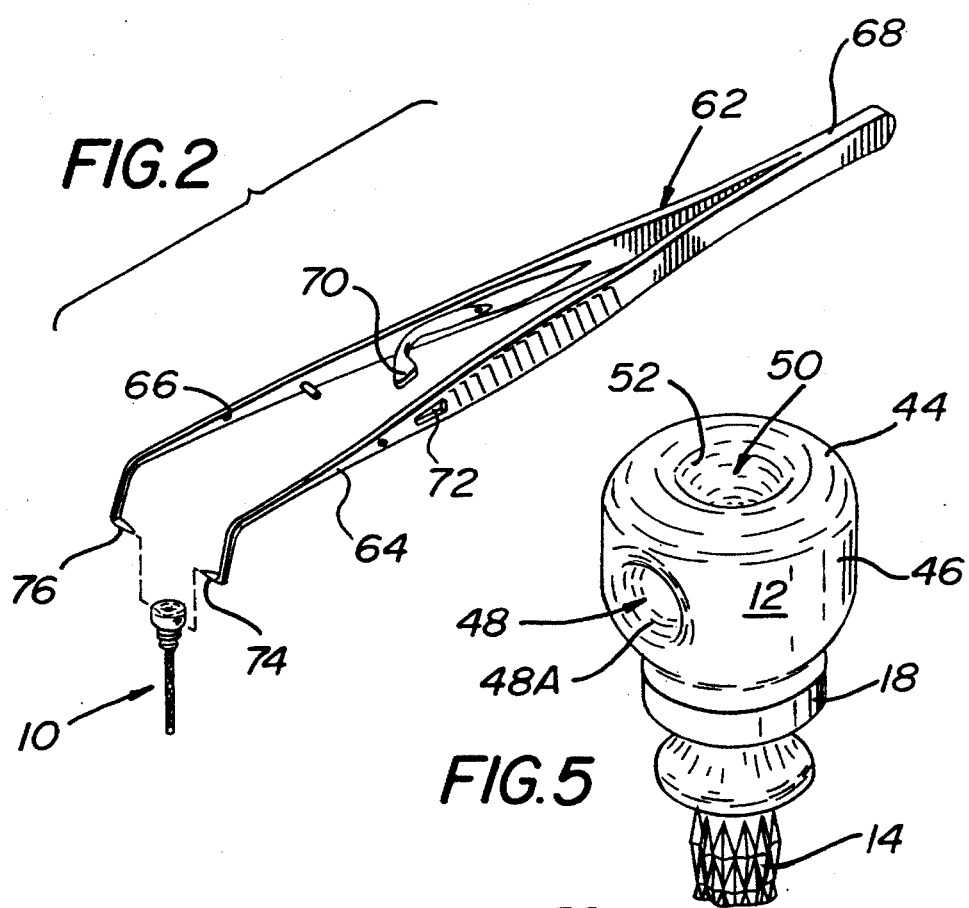
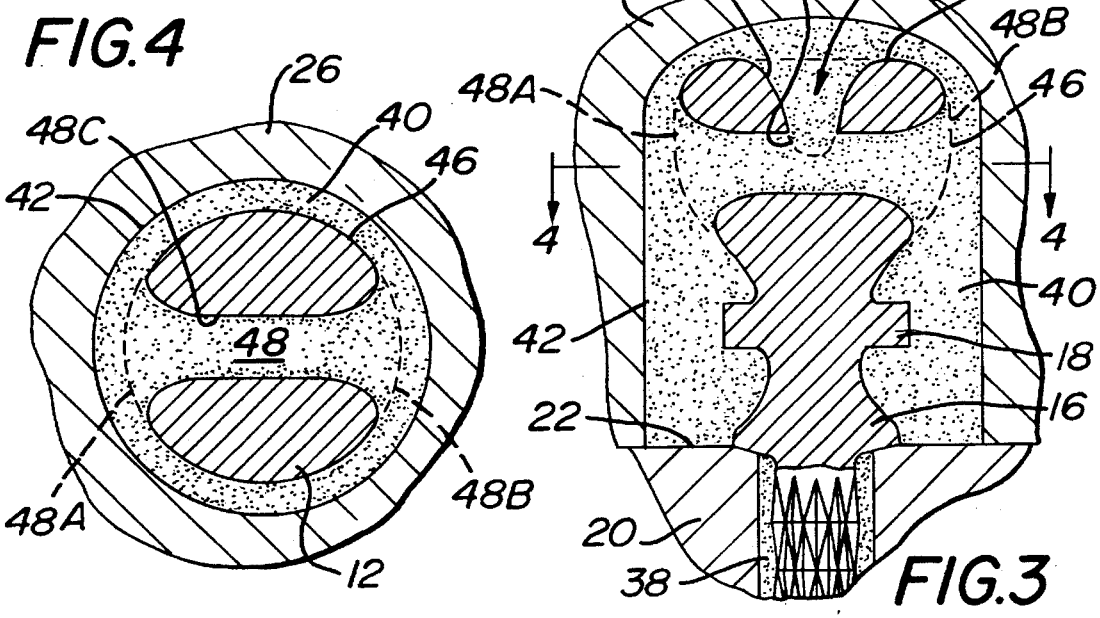

DENTAL POST WITH INTERNAL RETENTION MEANS

BACKGROUND OF THE INVENTION

This invention relates generally to dental appliances and more particularly to dental posts and devices used to handle dental posts.

It is well known in the field of dentistry to build up a dental restoration onto a tooth stub for replacement of missing dentition. The diseased or broken tooth is prepared leaving a tooth stub that provides a suitable support on which the restoration will be placed. After the root canal is cleaned and filled with the appropriate filling material it is partially reamed out to a proper size and depth forming a bore. A dental post is then selected and inserted into the prepared bore so that its shank substantially fills the bore while its head portion extends upwardly from the surface of the tooth stub. The post is retained within the bore using a suitable dental cement. Next, using a syringe or other dispensing means, a flowable dental core material is injected over the post head. The core material is formed and allowed to cure and harden on the post head to form a post-core buildup. Then, using a drill equipped with a high speed diamond burr, the post-core buildup is shaped to be fitted under a dental restoration, e.g., a porcelain or gold crown. Next, an impression is taken of the shaped post-core buildup which is used to fabricate the dental restoration. Finally, the dental restoration is fitted over the post-core buildup and cemented in place.

While numerous types of dental posts have provided improvements with respect to retention to and integration with core material, still further improvements would be beneficial so as to prevent accidental breaking off of the dental restoration after setting onto the dental post.

Some of the prior art posts utilized for such dental restorations contain enlarged heads or heads featuring indentations or dimples into which core material can flow. The difficulty with these prior art post designs is that because the indentations are not through openings, core material cannot flow deeply into the head portion and therefore cannot integrate as effectively with the post. By providing through openings in the post head in the present invention, a more effective integration between post head and core material will occur resulting in a stronger post-core buildup.

By way of example, U.S. Pat. Nos. 5,094,618 (Sullivan) and 5,073,112 (Weil) both show a dental post comprising a head portion featuring a pair of spheres with elongated indentations triangularly positioned thereon. Although such indentations may aid in providing some degree of retention between the dental post and core material, there is nothing set forth in either Sullivan or in Weil to suggest or indicate that the indentations are through openings that would permit core material to flow therethrough to facilitate a high degree of integration with the head portion of the dental post. Because the indentations are not through openings, the posts described therein appear to be unable to achieve an optimal degree of integration.

U.S. Pat. No. 4,752,225 (Bori) discloses a dental post having plural concave dimples on the surface of its head portion. According to Bori, the concave dimples help to hold a crown thereon by cement solidifying in the concave dimples. However, it appears that Bori does not show these dimples as through holes that would permit flow of core material through to the interior of the head section of the dental post so as to integrate the head portion with the core material. Further, it appears Bori does not disclose a head portion featuring a coronal opening (i.e., an opening in the top of the post head) which allows for the flow of an increased amount of core material to the interior of the head portion. Because Bori does not describe or show a coronal opening or a coronal rest seat it appears incapable of achieving a very high degree of post-core integration.

U.S. Pat. No. 4,622,012 (Smoler) discloses a dental post system that features an inner post which is inserted into an outer post that has been previously inserted into a prepared canal. The inner post has a flattened head portion that features a plurality of cutouts through which core material permeates to secure anchorage with the inner post head. The patent illustrates a number of different embodiments of the inner post head portion which in all cases is flattened with cut-outs provided thereon. Although these cutouts may provide some amount of integration of core material by allowing the material to flow through the cut-outs, because the head portion is flattened or thin, it appears to lack volume and therefore only a small amount of core material actually enters within the head portion for integration therein. Additionally, Smoler does not disclose a coronal opening which allows for an additional amount of core material to integrate within the post head.

U.S. Pat. No. 4,600,392 (Weissman) discloses a contoured dental post for retaining dental restorations onto a prepared tooth stub. In one embodiment, the dental post includes a transverse opening that extends through the upper end of the dental post. However, the dental post disclosed therein does not feature a coronal opening or a bulbous head portion containing a hollow volume that allows core material to flow therein and integrate with the bulbous head.

U.S. Pat. No. 4,778,388 (Sadayuki and Takashi) discloses a dental post comprising a shank that is insertable in a treated root canal and a head portion that extends above the tooth root. In one embodiment, the dental post is comprised of a cylindrical head portion featuring recesses and an axial bore extending through the head portion and shank of the dental post. Although these recesses may provide some amount of integration of core material by allowing the material to flow therein, there is nothing to suggest that these recesses are passageways that communicate with the axial bore to form an internal volume into which core material can flow to integrate with the dental post. These passageways appear to be present for gripping purposes for removing the dental post from the root canal. Further, none of the embodiments show a bulbous head.

U.S. Pat. 4,846,685 (Martin) discloses an embodiment of a dental post having a shank containing plural through bore holes arranged radially along the surface of the shank and a bore hole running along the central axis of the shank. The axial bore hole communicates with the radial bore holes so that as cement flows therein it locks the post from within and without into the tooth root and also acts as an anti-rotational device giving increased retention. The purpose of these bore holes is for the passage of cement therethrough in order to lock the post into the root canal. The structure in Martin does not appear to show the use of radial and axial bore holes in the post head for the purpose of passage of core material therethrough to integrate with the dental post. Additionally, the structure shown in Martin is cylindrical and is not comprised of a bulbous head.

In addition, many of the prior art dental posts utilize spiral threads, segments or lands located over the outer surface of the shank portion that cut into and deform the dentin of the tooth root upon insertion in order to achieve retention within the root canal. On many of these prior art dental posts, the threads or lands exert outward expansive forces to the tooth root and at times cause the same to fracture. Therefore, it is important to prevent the fracture of the tooth root during the insertion of the shank portion of a dental post thereinto, and even during the subsequent use of the tooth after the dental post and crown have been assembled to the root.

Therefore, the foregoing prior art dental posts, for reasons previously discussed, suffer from one or more drawbacks including poor integration with dental core material, poor adhesion to dental cement, risk of tooth root fracture during insertion of the post shank and high fabrication and installation costs.

OBJECTS OF THE INVENTION

Accordingly, it is a general object of the present invention to provide a dental post which overcomes the disadvantages of the prior art.

It is another object of this invention to provide a dental post that is simpler and less expensive to construct and install.

A further object of the present invention is to provide a dental post that will more effectively integrate with core material to form a stronger post-core buildup.

A further object of the present invention is to provide a dental post having improved retention capabilities with dental cement within a tooth root.

A further object of the present invention is to provide a dental post containing a coronal opening to improve integration with core material.

A further object of the present invention is to provide a dental post containing a shank that when inserted into a tooth root canal will result in minimal stress to the canal thus minimizing the risk of root fracture.

A further object of the present invention is to provide a dental post containing a means for dissipating lateral and occlusal forces away from the tooth root, thus minimizing the risk of root fracture.

A further object of the present invention is to provide a dental pliers for the safe handling and insertion of the dental post of the present invention.

SUMMARY OF THE INVENTION

This invention relates to a dental post for securely retaining a dental restoration on a prepared tooth stub having a top surface and a bore extending therein. The dental post comprises an enlarged head and a shank. The shank is an elongated rod-like member having a first longitudinal axis, with the outside diameter of the shank measured along a second axis perpendicular to the first axis and being a predetermined dimension. The enlarged head has a cross-sectional area which is greater than that of the shank. The shank is arranged to be fixedly secured within the bore so that the enlarged head extends beyond the top surface of the prepared tooth stub. The enlarged head has a passageway extending fully therethrough concentric with the second axis for receipt of a setable securement medium therein and about the surface of the head to secure the dental restoration to the post.

This invention also relates to a dental pliers for the safe handling and insertion of the dental post of the present invention. The dental pliers are comprised of a pair of opposing arms joined at a proximal end, each arm having a projection mounted at its distal end. The projections are diametrically opposed and facing inward and are shaped to fit within the open ends of the passageway extending through the bulbous head of the dental post.

BRIEF DESCRIPTION OF THE DRAWINGS

Other objects and many attendant features of this invention will become readily appreciated as the same becomes better understood by reference to the following detailed description when considered in connection with the accompanying drawing wherein:

FIG. 2 is an isometric view of the dental post of FIG. 1 shown for grasping by a pair of jaws of a dental pliers constructed in accordance with another aspect of this invention;

FIG. 3 is an enlarged sectional view taken along lines 3—3 of FIG. 1;

FIG. 4 is an enlarged sectional view taken along lines 4—4 of FIG. 3;

FIG. 5 is an enlarged isometric view of the bulbous head of the dental post of the present invention.

DETAILED DESCRIPTION OF THE PREFERRED EMBODIMENT

Figure 1:
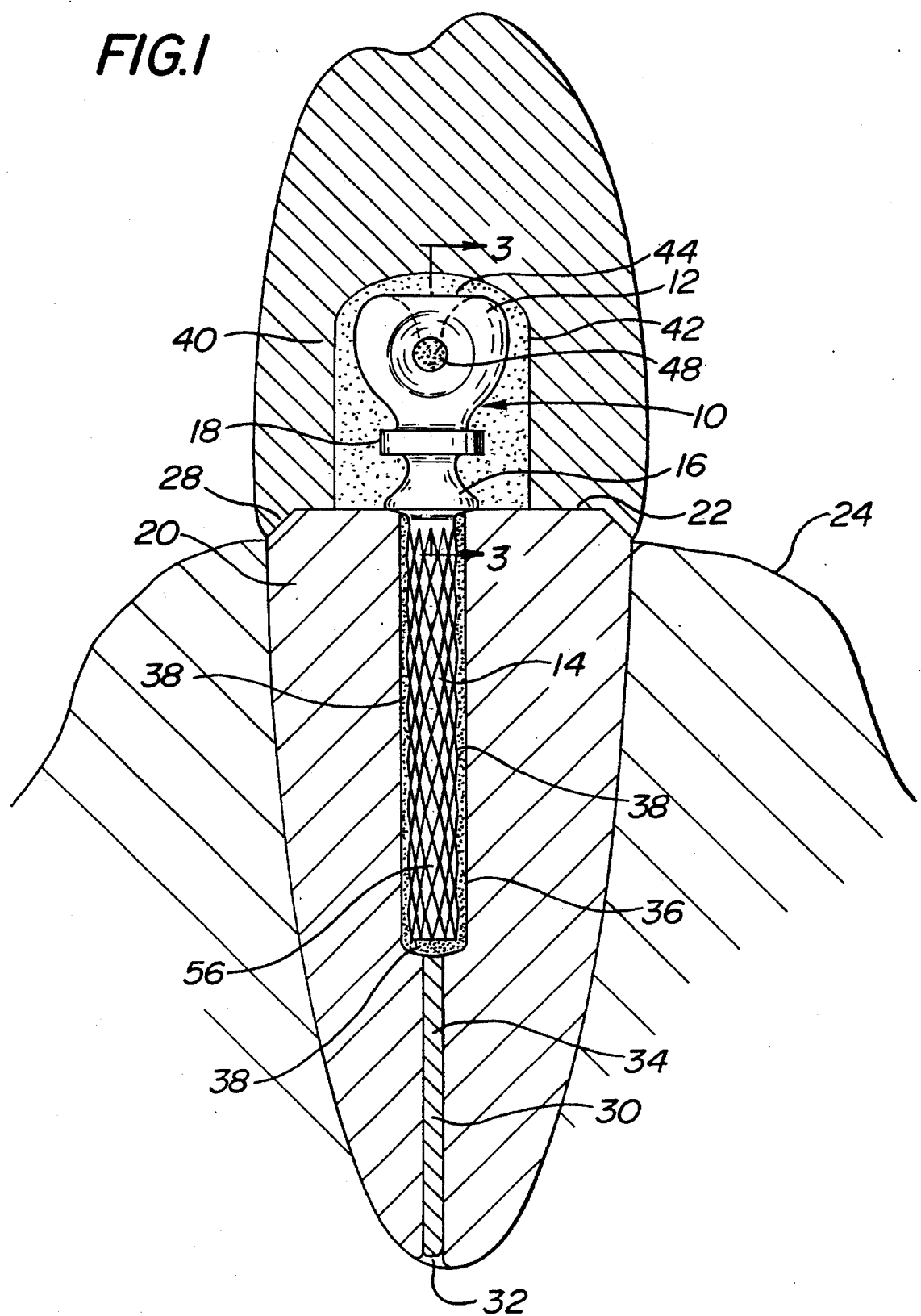
FIG. 1 is a sectional view of a finished dental restoration showing a prepared tooth stub and crown with the dental post of the present invention shown in full retained within the tooth stub using dental cement.

Referring now to the various figures of the drawings where like reference numerals refer to like parts, in FIG. 1 there is shown a dental post 10, constructed in accordance with this invention. The details of the dental post 10 will be described later. Suffice it for now to state that the dental post of the present invention is arranged to be inserted and retained within the root canal of an existing tooth stub to facilitate the build up of a dental restoration onto the tooth stub.

Referring to FIGS. 1, 3, 4 and 5, one exemplary embodiment of the dental post of the present invention is shown generally as 10 and comprises an enlarged or bulbous head 12 an elongated shank 14, a shoulder 16 and a strengthening flange 18. Although separately identified, the bulbous head, elongated shank, shoulder and strengthening flange are integrally connected and formed as a unitary structure. The dental post of the present invention is comprised of any suitable material, e.g., bio-compatible, machinable stainless steel.

Prior to the insertion of the dental post 10 into the tooth stub 20 as shown in FIG. 1, a suitable upper surface 22 somewhat above the gumline 24 is prepared to support a fitted dental restoration 26. Many times, the outer edge of the upper surface 22 is shaped to form a bevel 28 to facilitate attachment of the dental restoration 26. The particular tooth stub illustrated in FIG. 1 has a single root canal 30 extending downward to an apical opening 32. In order to retain the dental restoration 26 onto the tooth stub 20, there is required a dental post such as one of the present invention.

Prior to the placement of a dental post in the tooth root, the root canal 30 will be endodontically prepared in a manner well known to those skilled in the art through the use of endodontic files (not shown) to enlarge the root canal 30 by removing pulp material therefrom. The entire length of the root canal 30 is sealed with a suitable sealant 34, such as gutta percha. Next, drill bits (not shown) of successively larger sizes are utilized to enlarge the upper portion of the prepared root canal opening to form a dental post space 36. The dental post space 36 is comprised of a cylindrically shaped sidewall 36A that is enlarged to a diameter appropriate to receive the shank portion 14 of the dental post 10. Typically, the dental post space 36 extends approximately fifty to sixty (60) percent of the depth of the prepared tooth stub 20. The dental post space 36 provides a suitable receptacle for the dental post 10 which helps anchor the tooth restoration, i.e., crown 26. The prepared root canal 30 below the dental post space 36 and extending down to the apical opening 32 remains sealed with gutta percha 34.

A dental post 10 is then selected and inserted into dental post space 36 so that shank 14 substantially fills the dental post space 36. Once shank 14 is inserted, there should be adequate space around it so that cement 38 employed in this technique can flow in the annular space between the shank 14 and the wall 36A of dental post space 36 without creating hydraulic stresses. The post shank 14 is retained within the dental post space 36 using a suitable dental cement 38. After insertion of shank 14, the bulbous head 12 extends upwardly from the top surface 22 of the tooth stub 20. Using a syringe (not shown), a flowable setable dental core material 40 is injected over the bulbous head 12 and through a plurality of through openings contained therein. These plural openings will be described in further detail below. Once the core material 40 has set and hardened over the dental post 10, a structure is formed known as a post-core buildup 42. Next, using a drill equipped with a high speed diamond burr (not shown), the post-core buildup 42 is shaped to be fitted with the dental restoration 26. Next, an impression (not shown) is taken of the shaped post-core buildup 42 from which a dental restoration 26, such as a porcelain or gold crown is fabricated. Finally, the dental restoration 26 is fitted and cemented in place over the post-core buildup 42.

The bulbous head 12 of the dental post 10 is formed by any suitable means, e.g., stamping or swaging. The bulbous head 12 is provided in various outside diameter head sizes. That is, the dentist is able to select the appropriate head size based upon the amount of space available above the top surface 22 of tooth stub 20 for mounting dental restoration 26. For example, where a smaller tooth is being prepared for a crown and the amount of space on which to form a post-core buildup 42 is severely limited, it is necessary for the dentist to select a dental post 10 having a relatively small bulbous head 12 so that a sufficient amount of core material 40 can be formed thereover to build a strong post-core buildup 42. In such cases, it is necessary for the dentist to select a dental post 10 of the present invention having a relatively small bulbous head 12. In other instances, where there is little tooth structure above top surface 22 a dental post having a larger bulbous head is appropriate.

As shown in FIGS. 3, 4 and 5, the bulbous head 12 is comprised of a flat coronal surface 44, a sidewall 46, a transverse opening 48, a coronal opening 50 and a coronal rest seat 52. In FIG. 4, the sidewall 46 is shown as being generally circular and therefore having a diameter extending perpendicular to its longitudinal central axis of the post 10. The transverse opening 48 is an open passageway that extends diametrically through sidewall 46 perpendicular to the longitudinal central axis. As shown in FIGS. 1 and 5, transverse opening 48 is a circular through passageway and is located concentrically about the diameter of sidewall 46. As shown in FIGS. 3, 4 and 5, the transverse opening 48 is flared at ends 48A and 48B. By providing flared ends, 48A and 48B an increased volume of core material 40 can flow into transverse opening 48 in order to form a stronger post-core buildup. Additionally, flared ends 48A and 48B provide an escape route for trapped air within transverse opening 48.

The coronal opening 50 is an open passageway that extends downwardly from the coronal surface 44 and communicates with transverse opening 48 at an interface shown by phantom line 54 (FIG. 3). The coronal opening 50 is generally circular along its length and is concentric with the post axis (i.e., the central longitudinal axis). As the coronal opening 50 extends upward from transverse opening 48 toward coronal surface 44 it widens to form a coronal rest seat 52. The coronal rest seat 52 is cup-shaped and allows for an increased volume of core material 40 to flow into the coronal opening 50 to provide added stability and strength to the post-core buildup.

Although coronal opening 50 is illustrated in FIG. 3 as extending from coronal surface 44 to transverse opening 48, it should be understood that in accordance with an alternative embodiment of the present invention, the coronal opening 50 can extend from the coronal surface 44, through transverse opening 48 and extend further for a predetermined distance along the post axis through post shank 14 to provide increased volume into which core material 40 can flow to provide added stability and strength.

In addition, as shown in FIG. 1, in an alternative embodiment of the present invention, there is provided a shoulder 16 located above shank 14. In this embodiment, when dental post 10 is inserted in dental post space 36, the shoulder 16 abuts the upper surface 22 of the tooth stub 20. The shoulder 16 serves to dissipate lateral and occlusal, i.e., downward, forces away from tooth root 30, thereby preventing root fracture during chewing.

In accordance with the present invention, the dental post 10 is provided to the dental practitioner with a shank 14 of predetermined length that corresponds to respective drill sizes used in creating dental post space 36.

The shank 14 of the dental post is cylindrical in shape, having a constant cross-sectional diameter along its entire length.

According to the present invention, dental posts will be provided to the dentist in a variety of shank diameters, e.g., from 0.036 to 0.060 inches (0.914 to 1.524 mm) in diameter to assure a snug fit within variously sized dental post spaces 36, both narrow and wide. If the dental post space is relatively wide, a post containing a comparatively thick shank is selected for insertion therein. Conversely, if the dental post space 36 is narrow, a post containing a comparatively narrow shank is selected for insertion therein.

During chewing, the portion of dental post 10 extending above shoulder 16 is exposed to significant lateral forces. Where shank 14 is comparatively small in diameter, e.g., 0.036 to 0.040 inches (0.914 to 1.016 mm), these lateral forces can bend and break post 10 at any narrow point above shoulder 16. To provide reinforcement strength and thickness to the narrowest portion of dental post 10 extending above upper surface 22, the strengthening flange 18 is interposed between bulbous head 12 and shoulder 16. It should be understood that strengthening flange 18 is only necessary where shank 14 is comparatively small in diameter, e.g., 0.036 to 0.040 inches (0.914 to 1.016 mm). Where a dental post 10, constructed in accordance with this invention is comprised of a shank 14 having a larger diameter, e.g., 0.045 inches (1.143 mm) or larger the strengthening flange 18 is not necessary.

In the preferred embodiment of the present invention, the entire exterior surface of the shank 14 is comprised of a multitude of small planar facets 56 angularly oriented with respect to each other. By utilizing multiple angular facets 56, the surface area over the entire exterior surface of the shank 14 is maximized to provide superior bonding ability with cement upon insertion into the root canal. In this preferred embodiment, because the shank 14 is not threaded, it will not cut into dentin along the post space sidewall 36A, and will therefore avoid the risk of fracturing the tooth root during insertion. The multiple angular facets 56 can be provided along the exterior surface of the shank by a variety of methods, e.g., embossing.

Figure 6:
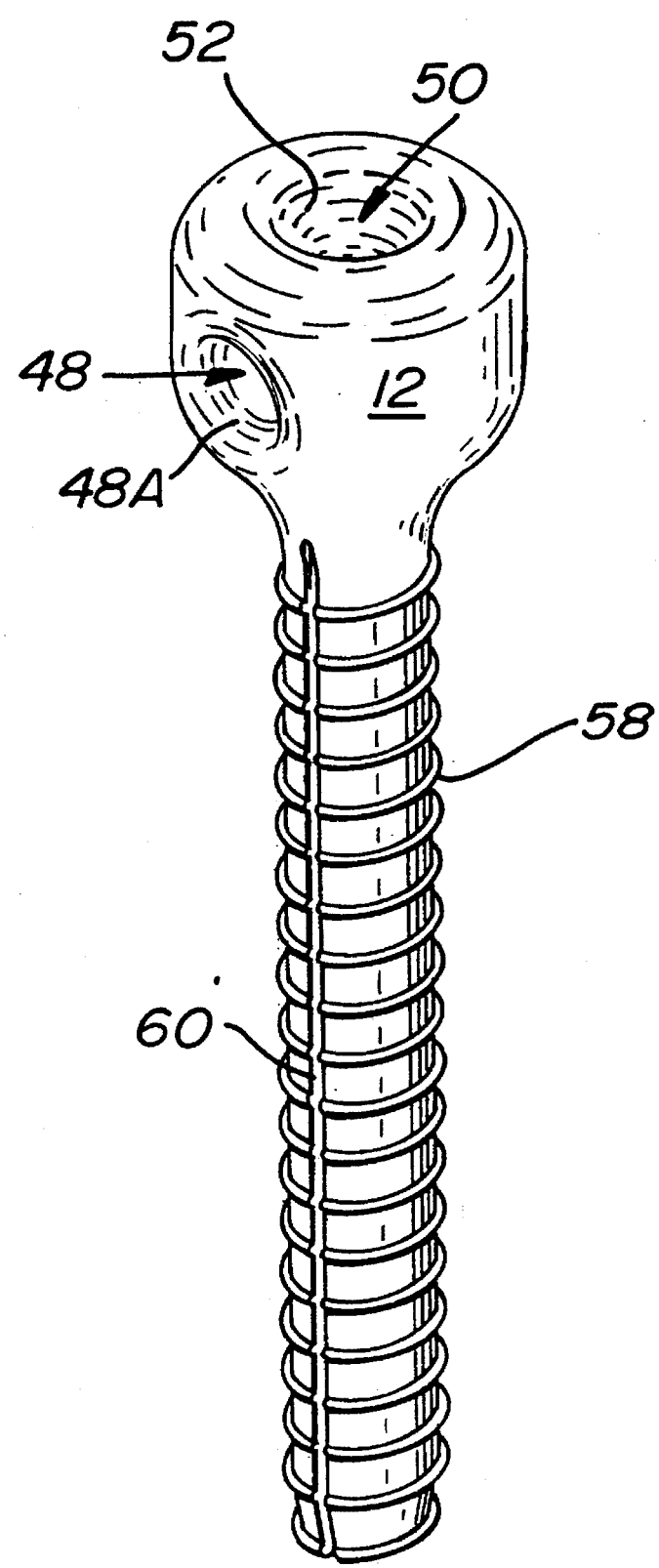
FIG. 6 is an enlarged isometric view of an alternative embodiment of the present invention.

Referring to FIG. 6, in an alternative embodiment of the present invention, shank 14 is provided with a continuous helical thread 58 and flute 60. The thread 58 is formed about the surface of shank 14 and extends over its entire length. The helical thread 58 has a very small pitch so as to maximize the number of revolutions the thread winds around shank 14. After application and cure of dental cement 38 between helical thread 58 and post space sidewall 36A, the shank 14 is securely anchored within the dental post space 36. This embodiment, utilizing a continuous helical thread 58 is less expensive to manufacture than the shank comprising multiple angular facets previously described in the preferred embodiment. The flute 60 extends longitudinally for a substantial length over shank 14 and serves to vent air, liquids or cement in the root canal during the insertion and seating of shank 14. The flute 60 also eliminates undesired pressure build-up and risk of tooth root fracture during insertion of shank 14. Although not shown in FIG. 6 the shoulder 16 and/or the strengthening flange 18 could be incorporated in this embodiment in accordance with this invention.

In FIG. 2, there is shown a hand-held dental pliers 62 modified in accordance with another aspect of this invention for safe handling and insertion of the dental post 10 of the present invention. Such hand-held dental pliers 62 are similar in construction and operation to dental pliers sold by various dental instrument retailers including the Henry Schein Company. Such hand-held pliers are comprised of a pair of arms 64 and 66 joined at one end to form a proximal handle 68. In accordance with this invention at the opposite end of each arm is a projection (to be described later) to enable the lifting of the dental post 10. In addition the hand-held pliers 62 are provided with a locking arm 70 and catch 72 to enable the practitioner to hold dental post 10 between arms 64 and 66 without applying pressure with thumb and forefinger.

As mentioned earlier the distal end of each arm 64 and 66 is provided with a pair of projections. These are designated by the reference numbers 74 and 76. The projections 74 and 76 are diametrically opposed and facing inwardly. The projections are conically shaped to fit within the flared ends 48A and 48B of transverse opening 48 to enable a dental practitioner to pick up and insert dental post 10 into dental post space 36 of prepared tooth stub 20.

In particular, to pick up dental post 10 using dental pliers 62 in accordance with this aspect of the present invention, the dental practitioner aligns projections 74 and 76 of dental pliers 62 with the flared ends 48A and 48B of transverse opening 48 and squeezes arms 64 and 66 with thumb and forefinger so that projections 74 and 76 enter flared ends 48A and 48B of transverse opening 48. Further squeezing will cause locking arm 70 to enter catch 72 to securely engage dental post 10 in dental pliers 62. With dental post 10 securely held in place between arms 74 and 76, the risk of losing grip of the dental post 10 during insertion into the dental post space 36 is greatly reduced.

It should be pointed out at this juncture that while the enlarged head is shown in the drawings as being bulbous, it may be of other shapes as well, e.g., cubic, so long as it includes the passageways as described heretofore.

Without further elaboration the foregoing will so fully illustrate my invention that others may, by applying current or future knowledge, adapt the same for use under various conditions of service.

I claim

1. A dental post for securely retaining a dental restoration on a prepared tooth stub having a top surface and a bore extending therein, said dental post comprising an enlarged head and a shank, said shank being an elongated rod-like member having a first longitudinal axis, with the outside diameter of a said shank measured along a second axis perpendicular to said first axis being a predetermined dimension, said enlarged head being of a cross-sectional area greater than that of said shank, said shank being arranged to be fixedly secured within said bore so that said enlarged head extends beyond the top surface of said prepared tooth stub, said enlarged head having a hole extending fully therethrough concentric with said second axis for receipt of a setable securement medium therein and about the surface of said enlarged head to secure said dental restoration to said post, said enlarged head additionally comprising an opening in said head concentric with said first axis and in communication with said hole for receipt of said setable securement medium therein to form a coronal seat for said dental restoration.

2. The dental post of claim 1 wherein said opening has a funnel shaped entrance.

3. The dental post of claim 1 wherein said shank includes a textured peripheral surface.

4. The dental post of claim 3 wherein said textured peripheral surface is multi-faceted.

5. The dental post of claim 1 wherein the surface of said shank includes a continuous helical thread.

6. The dental post of claim 5 wherein said shank includes a flute disposed longitudinally over a substantial length of said shank.

7. The dental post of claim 1 including an annular shoulder located above and adjacent to said shank for locating and suspending said dental post in a tooth root.

8. The dental post of claim 7 including a strengthening flange located above said annular shoulder and below said enlarged head.

9. A dental post for securely retaining a dental restoration on a prepared tooth stub having a top surface and a bore extending therein, said dental post comprising an enlarged head and a shank, said shank being an elongated rod-like member having a first longitudinal axis, with the outside diameter of said shank measured along a second axis perpendicular to said first axis being a predetermined dimension, said enlarged head being of a cross-sectional area greater than that of said shank, said shank being arranged to be fixedly secured within said bore so that said enlarged head extends beyond the top surface of said prepared tooth stub, said enlarged head having a passageway extending fully therethrough concentric with said second axis for receipt of a setable securement medium therein and about the surface of said enlarged head to secure said dental restoration to said post, said passageway having a pair of funnel shaped entrances, one at each end of said passageway.

10. The dental post of claim 9 wherein said shank includes a textured peripheral surface.

11. The dental post of claim 8 wherein said textured peripheral surface is multi-faceted.

12. The dental post of claim 9 including an annular shoulder located above and adjacent to said shank for suspending said dental post in a tooth root.

13. The detnal post of claim 12 including a strengthening flange located above said annular shoulder and below said enlarged head.

* * * * *